US00PP23426P2

(12) United States Plant Patent
Stemkens

(10) Patent No.: US PP23,426 P2
(45) Date of Patent: Feb. 26, 2013

(54) ***LEUCANTHEMUM* PLANT NAMED 'LEUZ0001'**

(50) Latin Name: *Leucanthemum maximum*
Varietal Denomination: LEUZ0001

(75) Inventor: Henricus Godefridus Wilhelmus Stemkens, Andijk (NL)

(73) Assignee: Syngenta Crop Protection AG, Basal (CH)

( * ) Notice: Subject to any disclaimer, the term of this patent is extended or adjusted under 35 U.S.C. 154(b) by 0 days.

(21) Appl. No.: 13/506,273

(22) Filed: Apr. 7, 2012

(51) Int. Cl.
*A01H 5/00* (2006.01)

(52) U.S. Cl. ..... Plt./285; Plt./284

(58) Field of Classification Search ..... Plt./285, Plt./284
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Leucanthemum* plant named 'LEUZ0001', characterized by its compact, upright and mounded plant habit; freely branching habit; strong and upright flowering stems; early and freely flowering habit; and large semi-double inflorescences with white-colored ray florets.

1 Drawing Sheet

Botanical designation: *Leucanthemum maximum.*
Cultivar denomination: 'LEUZ0001'.

BACKGROUND OF THE INVENTION

The present invention relates to a new and distinct cultivar of *Leucanthemum* plant, botanically known as *Leucanthemum maximum* and hereinafter referred to by the name 'LEUZ0001'.

The new *Leucanthemum* plant is a product of a planned breeding program conducted by the Inventor in Enkhuizen, The Netherlands. The objective of the breeding program is to create new compact semi-double *Leucanthemum* plants that flower early and for a long period of time without a vernalization requirement.

The new *Leucanthemum* plant originated from a cross-pollination conducted by the Inventor on Aug. 15, 2006 in Enkhuizen, The Netherlands of a proprietary selection of *Leucanthemum maximum* identified as code number F2764-1, not patented, as the female, or seed, parent with a proprietary selection of *Leucanthemum maximum* identified as code number F2772-5, not patented, as the male, or pollen, parent. The new *Leucanthemum* plant was discovered and selected by the Inventor as a single flowering plant in a controlled environment in Enkhuizen, The Netherlands on Jul. 16, 2007.

Asexual reproduction of the new *Leucanthemum* plant by terminal cuttings in a controlled greenhouse environment in Enkhuizen, The Netherlands since Sep. 17, 2007 has shown that the unique features of this new *Leucanthemum* plant are stable and reproduced true to type in successive generations.

SUMMARY OF THE INVENTION

Plants of the new *Leucanthemum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'LEUZ0001'. These characteristics in combination distinguish 'LEUZ0001' as a new and distinct *Leucanthemum* plant:

1. Compact, upright and mounded plant habit.
2. Freely branching habit.
3. Strong and upright flowering stems.
4. Early and freely flowering habit.
5. Large semi-double inflorescences with white-colored ray florets.

Plants of the new *Leucanthemum* differ primarily from plants of the female parent selection in the following characteristics:

1. Plants of the new *Leucanthemum* are more compact than plants of the female parent selection.
2. Plants of the new *Leucanthemum* have darker green-colored leaves than plants of the female parent selection.
3. Plants of the new *Leucanthemum* have semi-double inflorescences whereas plants of the female parent selection have double inflorescences.

Plants of the new *Leucanthemum* differ primarily from plants of the male parent selection in the following characteristics:

1. Plants of the new *Leucanthemum* are more freely branching than plants of the male parent selection.
2. Plants of the new *Leucanthemum* have smaller inflorescences than plants of the male parent selection.
3. Plants of the new *Leucanthemum* have semi-double inflorescences whereas plants of the male parent selection have single inflorescences.

Plants of the new *Leucanthemum* can be compared to plants of *Leucanthemum* 'LaCrosse', not patented. In side-by-side comparisons, plants of the new *Leucanthemum* differ from plants of 'LaCrosse' in the following characteristics:

1. Plants of the new *Leucanthemum* flower earlier than plants of 'LaCrosse'.
2. Inflorescences of plants of the new *Leucanthemum* had broader and longer ray florets than plants of 'LaCrosse'.

BRIEF DESCRIPTION OF THE PHOTOGRAPHS

The accompanying colored photographs illustrate the overall appearance of the new *Leucanthemum* plant showing the colors as true as it is reasonably possible to obtain in colored reproductions of this type. Colors in the photographs may differ slightly from the color values cited in the detailed botanical description which accurately describe the colors of the new *Leucanthemum* plant.

The photograph at the bottom of the sheet comprises a side perspective view of a typical flowering plant of 'LEUZ0001' grown in a container.

The photograph at the top of the sheet comprises a close-up view of typical inflorescences of 'LEUZ0001'.

DETAILED BOTANICAL DESCRIPTION

The aforementioned photographs and following observations and measurements describe plants grown in one-gallon containers during the winter in a polyethylene-covered greenhouse in Lancaster, Pa. and under cultural practices typical of commercial *Leucanthemum* production. During the production of the plants, day temperatures ranged from 18° to 29° C. and night temperatures averaged 18° C. Plants were 20 weeks old when the photographs and the description were taken. In the following description, color references are made to The Royal Horticultural Society Colour Chart, 2007 Edition, except where general terms of ordinary dictionary significance are used.

Botanical classification: *Leucanthemum maximum* 'LEUZ0001'.

Parentage:

*Female, or seed, parent*.—Proprietary selection of *Leucanthemum maximum* identified as code number F2764-1, not patented.

*Male, or pollen, parent*.—Proprietary selection of *Leucanthemum maximum* identified as code number F2772-5, not patented.

Propagation:

*Type*.—Terminal vegetative cuttings.

*Time to initiate roots, summer*.—About six days at 20° C.

*Time to initiate roots, winter*.—About seven days at 20° C.

*Time to produce a rooted young plant, summer*.—About 16 days at 20° C.

*Time to produce a rooted young plant, winter*.—About 18 days at 20° C.

*Root description*.—Medium in thickness, fibrous; white in color.

*Rooting habit*.—Freely branching, dense.

Plant description:

*Appearance/growth habit*.—Herbaceous perennial; compact, upright and mounded plant habit; moderately vigorous to vigorous growth habit; freely branching habit with about 26 basal branches developing per plant.

*Plant height*.—About 14.8 cm.

*Plant width*.—About 25.3 cm.

*Basal branch description*.—Aspect: Upright. Strength: Strong. Length: About 12.5 cm. Diameter: About 5 mm. Internode length: Before flowering, about 8 mm; when flowering, about 1.7 cm. Texture: Pubescent; longitudinally ridged. Color: Close to 138B.

*Foliage description*.—Arrangement: Alternate; simple; sessile. Length: About 6.8 cm to 8.5 cm. Width: About 1.2 cm to 1.4 cm. Shape: Narrowly spatulate. Apex: Broadly acute. Base: Attenuate; clasping. Margin: Dentate to serrate. Texture, upper and lower surfaces: Smooth, glabrous; margins, sparsely pubescent. Venation pattern: Pinnate, reticulate. Color: Developing leaves, upper and lower surfaces: Close to 146B. Fully developed leaves, upper surface: Close to 147A; venation, close to 146B. Fully developed leaves, lower surface: Close to 146A; venation, close to 146B.

Inflorescence description:

*Appearance*.—Semi-double inflorescence form with frilled ray florets and tubular disc florets; inflorescences held upright on strong peduncles; ray and disc florets develop acropetally on a capitulum.

*Fragrance*.—None to slightly sour.

*Flowering response*.—Plants begin flowering about seven to nine weeks after planting, no requirement for vernalization; long flowering period, plants flower naturally from mid-June until the autumn in Pennsylvania.

*Postproduction longevity*.—Inflorescences maintain good substance for about ten to twelve days on the plant; inflorescences persistent.

*Quantity of inflorescences*.—Freely flowering habit, about 22 to 26 inflorescences develop per plant.

*Inflorescence size*.—Diameter: About 7.5 cm. Depth (height): About 1.8 cm. Disc diameter: About 2.4 cm. Receptacle height: About 6 mm. Receptacle diameter: About 3.2 cm.

*Inflorescence buds*.—Shape: Flattened sphere. Height: About 1.2 cm. Diameter: About 1.7 cm. Color: Close to 155A.

*Ray florets*.—Length: About 3.1 cm. Width: About 7 mm. Shape: Outer ray florets, oblong; inner ray florets, deeply incised or curled over outer disc florets. Apex: Irregularly emarginate, fringed. Base: Attenuate. Margin: Entire. Texture, upper and lower surfaces: Smooth, glabrous; velvety; longitudinally ridged. Number per inflorescence: About 100 arranged in about four to five whorls. Color: When opening, upper and lower surfaces: Close to 155D. Fully opened, upper and lower surfaces: Close to NN155D.

*Disc florets*.—Shape: Fused tubular, erect and elongated. Apex: Acute. Length: About 8 mm. Diameter: About 1.5 mm. Number per inflorescence: About 440 massed at the center of the receptacle. Color, when opening: Apex: Close to 11A. Mid-section: Close to 15A. Base: Close to 145A. Color, fully opened: Apex: Close to 12A. Mid-section: Close to 15C. Base: Close to 145A.

*Involucral bracts*.—Length: About 7 mm. Width: About 2 mm. Shape: Lanceolate. Apex: Acute. Base: Truncate. Margin: Entire. Texture, upper and lower surfaces: Smooth, glabrous; margins, membranous. Number per inflorescence: About 28 arranged in three to four whorls. Color, upper surface: Close to 144D. Color, lower surface: Close to 138B.

*Peduncles*.—Length: About 3.7 cm. Diameter: About 3 mm. Strength: Strong. Angle: Upright. Texture: Pubescent; longitudinally ridged. Color: Close to 137C.

*Reproductive organs*.—Androecium: Present on disc florets only. Quantity per floret: Five per disc floret. Filament length: About 1.5 mm. Filament color: Close to 145B. Anther shape: Oblong. Anther length: About 1.5 mm. Anther color: Close to 15A. Pollen amount: Scarce. Pollen color: Close to 17B. Gynoecium: Present on ray and disc florets. Quantity per floret: One. Pistil length: About 7 mm. Stigma shape: Bi-parted. Stigma color: Close to 4A. Style length: About 3 mm. Style color: Close to 145D. Ovary color: Close to 145C.

*Seeds and fruits*.—Seed and fruit production have not been observed on plants of the new *Leucanthemum*.

Disease & pest resistance: Plants of the new *Leucanthemum* have not been observed to be resistant to pathogens and pests common to *Leucanthemum* plants.

Garden performance: Plants of the new *Leucanthemum* have been observed to have good garden performance and to tolerate wind and rain, to be hardy to USDA Hardiness Zone 5 and tolerant to AHS Heat Zone 8-1.

It is claimed:

1. A new and distinct *Leucanthemum* plant named 'LEUZ0001' as illustrated and described.

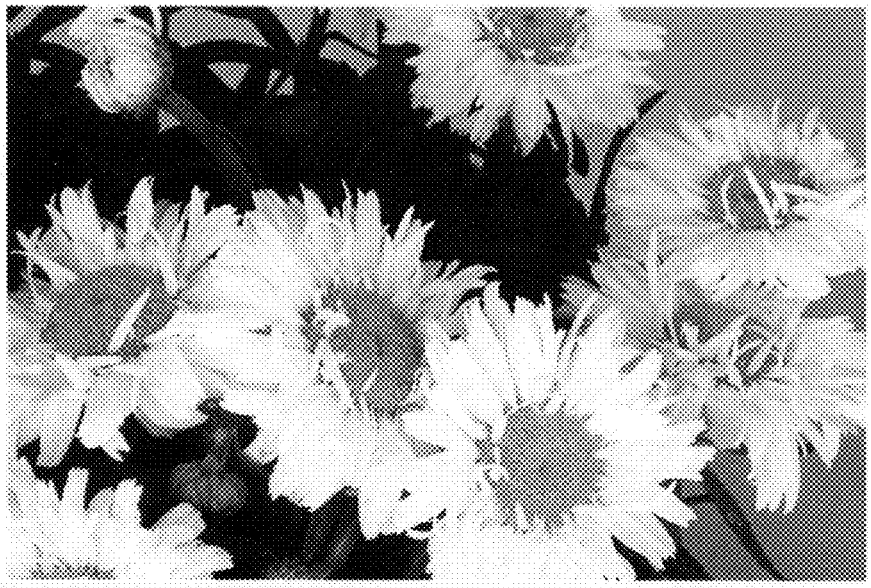
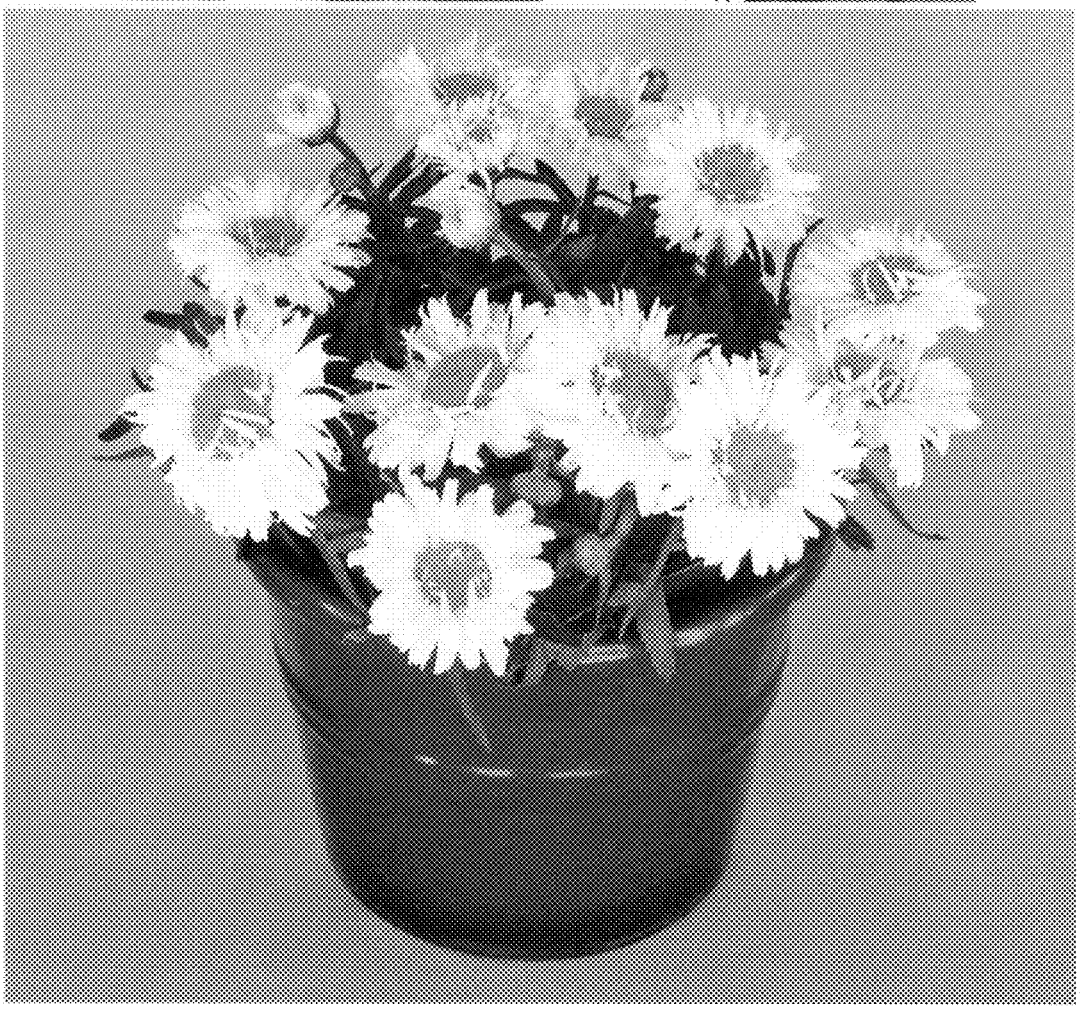

* * * * *